United States Patent [19]

McLeod

[11] 4,318,406
[45] Mar. 9, 1982

[54] COLOSTOMY OR ILEASTOMY APPLICANCE

[75] Inventor: Patrick H. McLeod, London, England

[73] Assignee: Matburn (Holdings) Limited, London, England

[21] Appl. No.: 60,177

[22] Filed: Jul. 24, 1979

Related U.S. Application Data

[63] Continuation of Ser. No. 811,531, Jun. 30, 1977, abandoned.

[30] Foreign Application Priority Data

Jul. 6, 1976 [GB] United Kingdom ............... 27976/76

[51] Int. Cl.³ .............................................. A61F 5/44
[52] U.S. Cl. .................................................. 128/283
[58] Field of Search ..................... 128/283, 275, 295; 55/387, 389, 364, 486, 316; 4/306

[56] References Cited

U.S. PATENT DOCUMENTS

| 2,826,265 | 3/1958 | De Woody | 55/486 |
| 3,492,998 | 2/1970 | Mascaro | 55/387 |
| 3,521,630 | 7/1970 | Westberg | 128/206.15 |
| 3,575,170 | 4/1971 | Clark | 128/275 |
| 3,690,320 | 9/1972 | Riely | 128/283 |
| 3,759,260 | 9/1973 | Nolan et al. | 128/283 |
| 3,892,617 | 7/1975 | DePriest | 128/132 D |
| 3,952,727 | 4/1976 | Nolan | 128/283 |
| 3,998,255 | 12/1976 | Mather et al. | 128/275 |

FOREIGN PATENT DOCUMENTS

| 1343882 | 1/1974 | United Kingdom ............... 128/295 |
| 1376888 | 12/1974 | United Kingdom . | |

Primary Examiner—C. Fred Rosenbaum
Attorney, Agent, or Firm—McAulay, Fields, Fisher, Goldstein & Nissen

[57] ABSTRACT

A filter is provided for a colostomy or ileostomy bag. The filter has a first layer of material which is gas permeable and water impermeable and forms the gas inlet side of the filter, a second layer of material which is gas permeable or is rendered gas permeable by the presence of at least one aperture therethrough. A layer of carbon cloth is sandwiched between the first and second layers, the first and second layers being secured to the carbon cloth by a weld which extends through the periphery of the carbon cloth.

7 Claims, 2 Drawing Figures 4,318,406

1

COLOSTOMY OR ILEASTOMY APPLIANCE

This is a continuation of application Ser. No. 811,531, filed June 30, 1977, and now abandoned.

FIELD OF THE INVENTION

This invention relates to a filter for use in venting a colostomy or ileostomy bag, and a method of making such a filter.

BACKGROUND OF THE INVENTION

When colostomy and ileostomy bags are used there is often a build up of flatus and it is desirable to include some means for releasing this. However, if a vent is provided it should also include a means for removing the unpleasant odours from the flatus. A number of ways of achieving this have been proposed in the past, including the use of a filter containing carbon particles or granules on a support. A disadvantage of this type of filter is that a long pathway is needed through the carbon for the filter to be effective.

BRIEF DESCRIPTION OF THE INVENTION

According to the present invention there is provided a filter for a colostomy or ileostomy bag, which comprises a first layer of material which is gas permeable and water impermeable and forms the gas inlet side of the filter, a second layer of material which is gas permeable or is rendered gas permeable by the presence of at least one aperture therethrough, and a layer of carbon cloth sandwiched between the said first and second layers, the said first and second layers being secured to the carbon cloth by a weld which extends through the periphery of the carbon cloth.

Figure 1:
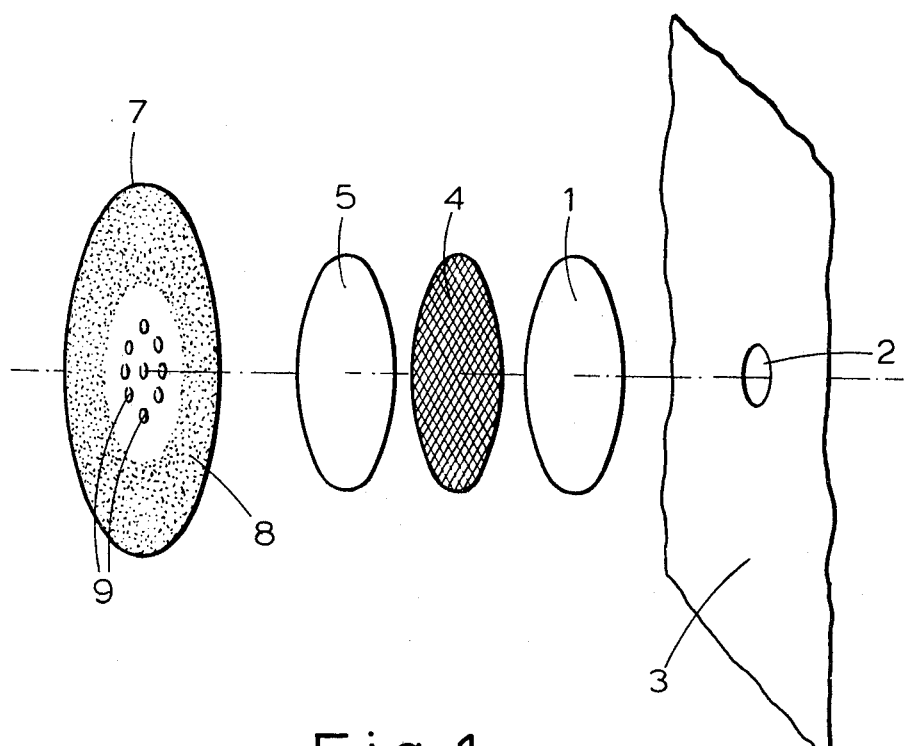
FIG. 1 is an exploded perspective view of one embodiment of a filter according to the invention in position on a colostomy or ileostomy bag.

The filter shown in FIG. 1 comprises on the gas inlet side thereof a film 1 of material which is gas permeable but water impermeable, such as a form of "Tyvek", which, in use, fits directly over a vent 2 in a face of the bag 3 (part of which is shown). The name "Tyvek" denotes a range of spun-bonded plastics materials, some of which are impermeable to water and some of which are not. A carbon cloth 4 which is placed on the "Tyvek" layer 1 covered by another film 5 also of "Tyvek" which is gas permeable and may or may not be water impermeable. Alternatively, the film 5 may be of gas impermeable material in which case it is provided with at least one aperture therethrough. An outer layer 7 is used to secure the filter to the outside of the bag 3. The means for securing the filter to the bag may either be a layer 8 of adhesive (as illustrated), or it may be a weld if the outer layer is made of a suitable material such as polyvinylchloride or polyvinyldichloride. If the outer layer is so arranged that it covers all the carbon filter it is necessary to provide a suitable area of it, with perforations 9, unless the outer layer is of a gas permeable material. In the latter case the film of which the outer layer is made is at least as permeable and preferably even more gas permeable than the film which fits directly over the vent. Alternatively, the outer layer may just be a means of securing the outer edge of the filter to the bag, for example an adhesive annular ring.

The layers 1,4 and 5 are secured together by an annular weld which passes through the layer 4 and extends to the periphery thereof. The fact that the weld extends to the periphery of the layer of carbon cloth 4 means that once the weld is formed the risk of carbon cloth fraying from the edges thereof is much reduced. A method of achieving a comparable result with the embodiment of FIG. 2 is known.

Figure 2:
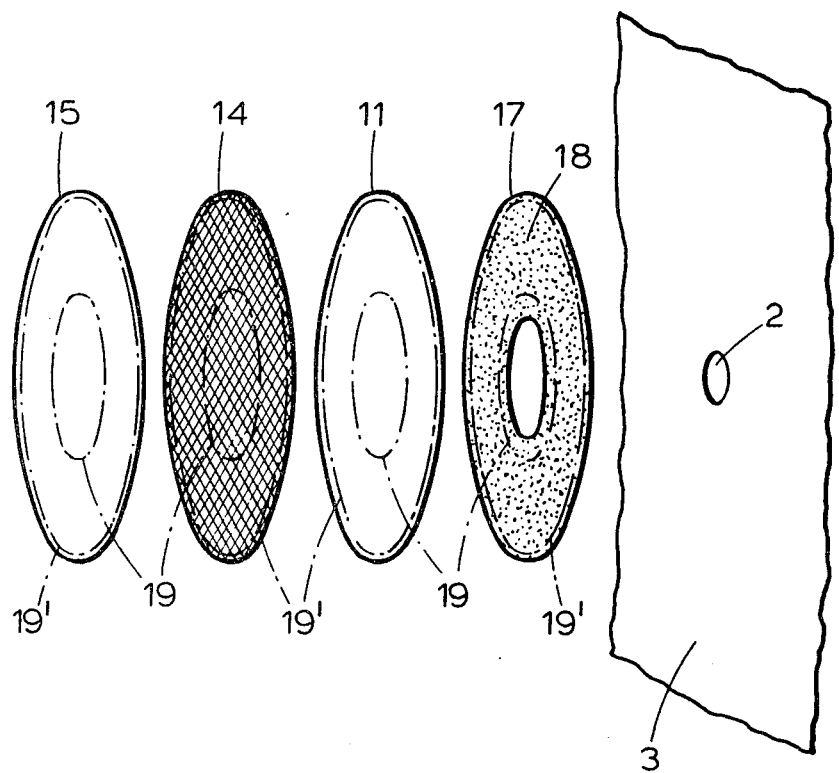
FIG. 2 is a similar view of a second embodiment of filter.

The filter shown in FIG. 2 comprises a layer of carbon cloth 14 sandwiched between two layers 11 and 15 of "Tyvek". Between the layer 11 and the bag 3 is a film of polyethylene 17 having a layer 18 of adhesive thereon. The layers 11,14,15 and 17 are secured together by concentric annular welds 19 and 19'. Although the welds are indicated by lines they would in practice have a finite width, and the weld 19' extends to the periphery of the layers 11,14,15 and 17.

Preferably the filter is secured to the outside of the bag, although it would alternatively be possible to secure it to the inside of the bag. In either case the water impermeable layer is on the gas inlet side of the filter, that is to say if the filter is on the outside of the bag the water impermeable layer is adjacent the bag, whilst if the filter is on the inside of the bag, the water impermeable layer is remote from the bag. This means that liquid from the bag cannot enter the carbon cloth.

The vent to which the filter is secured can be on either of the faces of the bag, but it is preferably on the same face as the stoma hole and preferably located above the stoma hole.

If desired, the filter may comprise a plurality of layers of carbon cloth, the filter having alternate layers of carbon cloth and material which is gas permeable or rendered gas permeable by the presence of apertures therethrough.

An example of a suitable carbon cloth is disclosed in U.K. Pat. No. 1,301,101. It is to be understood that the term "carbon cloth" as used herein refers to an activated carbon cloth which may be woven or non-woven.

I claim:

1. An ostomy bag having a vent opening and a filter for removing odors from gases exiting through the vent, secured to the bag so as to cover the vent opening, the filter comprising a first layer of weldable material which is gas permeable and water impermeable, the first layer being in contact with the interior of the bag so as to form the gas inlet side of the filter, a second outer layer of weldable material which is gas permeable and water impermeable, and a layer of activated carbon fiber cloth sandwiched between the first and second layers which form an envelope therefor completely enveloping the surfaces of said carbon fiber cloth, the first and second layers and carbon cloth layer being secured together by an annular weld extending between the first and second layers and passing through the carbon cloth, including the outer periphery of the barbon cloth thus eliminating passage of gas around the edges of said carbon cloth.

2. A bag as claimed in claim 1, wherein the said first and second layers are of a spun-bonded material.

3. A bag as claimed in claim 1, wherein the said first and second layers and the layer of carbon cloth are of the same size as one another and have aligned edges.

4. A bag as claimed in claim 1, wherein the filter further comprises a cover layer of larger area than both the said first and second layers, the cover layer having a face which is secured to the said second layer so that its periphery overlaps edges of the said first and second layers.

5. A bag as claimed in claim 4, wherein the said face has a layer of adhesive thereon.

6. A bag as claimed in claim 1, wherein the filter further comprises an apertured backing layer having one face secured to the said first layer and the opposite face provided with a layer of adhesive.

7. A bag as claimed in claim 1, wherein the filter comprises a plurality of layers of carbon cloth, the filter having alternate layers of carbon cloth and material which is gas permeable or rendered gas permeable by the presence of apertures therethrough.

* * * * *